(12) United States Patent
Yoo et al.

(10) Patent No.: US 11,889,917 B2
(45) Date of Patent: Feb. 6, 2024

(54) SHOE MANAGEMENT APPARATUS

(71) Applicant: LG ELECTRONICS INC., Seoul (KR)

(72) Inventors: Hyunsun Yoo, Seoul (KR); Jeong Guen Choi, Seoul (KR); Joohyeon Oh, Seoul (KR); Jae Myung Lim, Seoul (KR); Byoungjoon Han, Seoul (KR); Sang Yoon Lee, Seoul (KR); Hyunju Kim, Seoul (KR); Jeaseok Seong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 100 days.

(21) Appl. No.: 17/356,218

(22) Filed: Jun. 23, 2021

(65) Prior Publication Data

US 2021/0401169 A1 Dec. 30, 2021

(30) Foreign Application Priority Data

| Jun. 24, 2020 | (KR) | .......................... | 10-2020-0077410 |
| Jun. 24, 2020 | (KR) | .......................... | 10-2020-0077411 |
| Jun. 24, 2020 | (KR) | .......................... | 10-2020-0077412 |
| Jun. 24, 2020 | (KR) | .......................... | 10-2020-0077413 |
| Jun. 24, 2020 | (KR) | .......................... | 10-2020-0077414 |
| Jun. 24, 2020 | (KR) | .......................... | 10-2020-0077415 |
| Jun. 24, 2020 | (KR) | .......................... | 10-2020-0077417 |
| Dec. 8, 2020 | (KR) | .......................... | 10-2020-0170566 |
| Mar. 9, 2021 | (KR) | .......................... | 10-2021-0031064 |

(51) Int. Cl.
*A47B 61/04* (2006.01)
*F24F 7/007* (2006.01)
*A61L 2/08* (2006.01)
*A61L 2/07* (2006.01)
*A61L 2/10* (2006.01)

(52) U.S. Cl.
CPC ................ *A47B 61/04* (2013.01); *A61L 2/07* (2013.01); *A61L 2/088* (2013.01); *A61L 2/10* (2013.01); *F24F 7/007* (2013.01)

(58) Field of Classification Search
CPC ... A47B 61/04; A61L 2/07; A61L 2/10; A61L 2/088; F24F 7/007; F24F 13/10
USPC .................................................. 312/213, 107
See application file for complete search history.

(56) References Cited

U.S. PATENT DOCUMENTS

| 1,362,101 | A | * | 12/1920 | Hillman | ................ | F25D 23/065 |
| | | | | | | 62/417 |
| 2,444,887 | A | * | 7/1948 | Wyeth | ..................... | F25D 23/12 |
| | | | | | | 62/409 |

(Continued)

FOREIGN PATENT DOCUMENTS

| CN | 107044483 A | 8/2017 |
| JP | 2002-177374 A | 6/2002 |

(Continued)

*Primary Examiner* — James O Hansen
(74) *Attorney, Agent, or Firm* — Birch, Stewart, Kolasch & Birch, LLP

(57) ABSTRACT

A shoe management apparatus including a cabinet including an inner space for storing shoes, an exhaust port disposed at a rear surface of the inner space and discharging air into the inner space, and a front discharge port disposed at an upper surface of the cabinet and discharging air from the inner space to outside of the shoe management apparatus.

11 Claims, 9 Drawing Sheets

(56) References Cited

U.S. PATENT DOCUMENTS

| | | | | |
|---|---|---|---|---|
| 5,369,892 A | * | 12/1994 | Dhaemers | F26B 21/00 |
| | | | | 34/224 |
| 8,763,414 B2 | * | 7/2014 | Carlson | H05K 7/20745 |
| | | | | 52/220.2 |
| 2005/0109643 A1 | * | 5/2005 | Huang | A61L 2/202 |
| | | | | 206/278 |
| 2008/0252189 A1 | * | 10/2008 | Regan | A47B 87/0223 |
| | | | | 312/249.8 |
| 2017/0244262 A1 | | 8/2017 | Schadow et al. | |
| 2021/0071345 A1 | | 3/2021 | Lee et al. | |

FOREIGN PATENT DOCUMENTS

| | | |
|---|---|---|
| KR | 20-0286953 Y1 | 8/2002 |
| KR | 10-0590794 B1 | 6/2006 |
| KR | 10-2008-0105499 A | 12/2008 |
| KR | 10-2019-0128460 A | 11/2019 |

* cited by examiner

[FIG. 1]
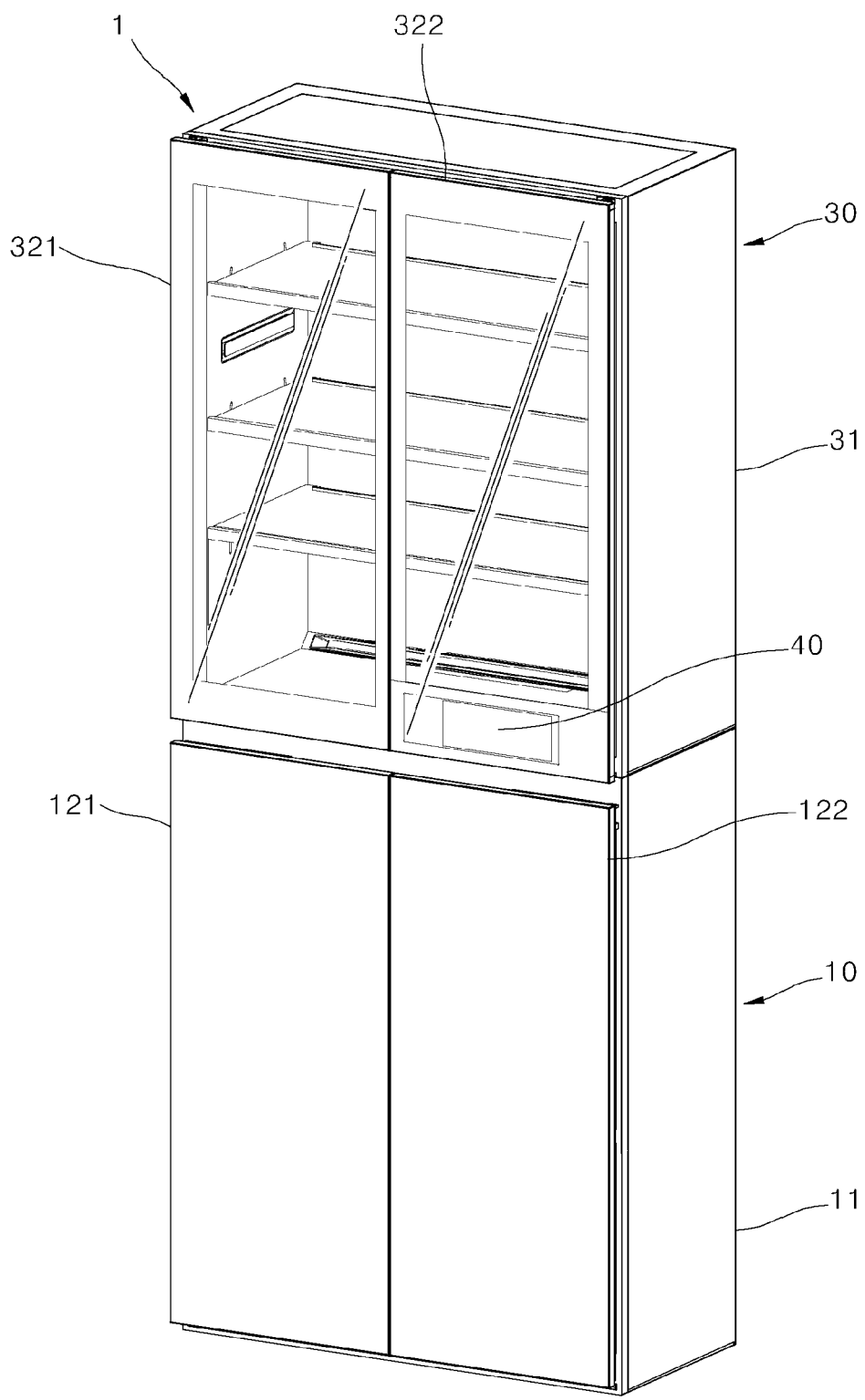

[FIG. 2]
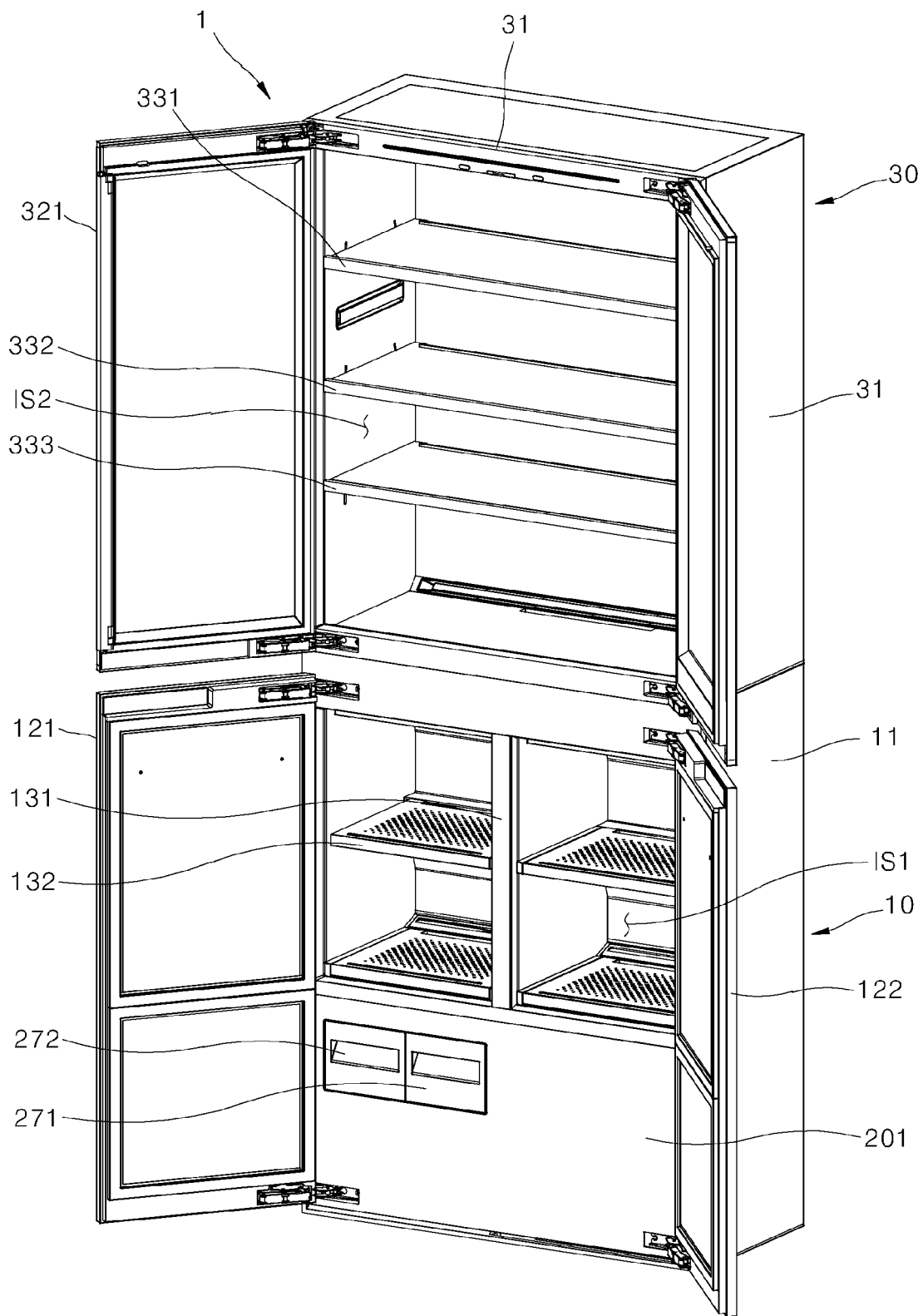

[FIG. 3]
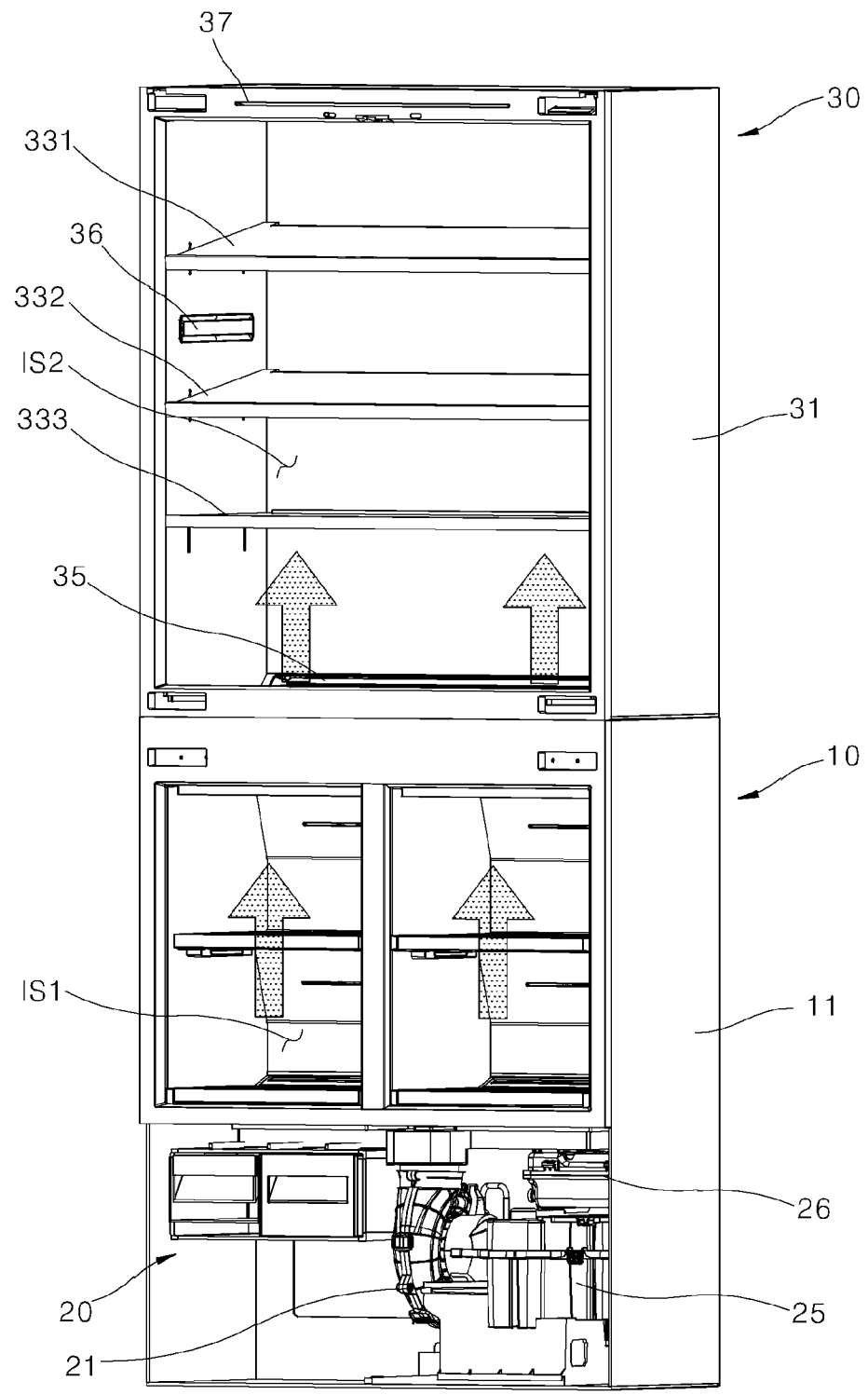

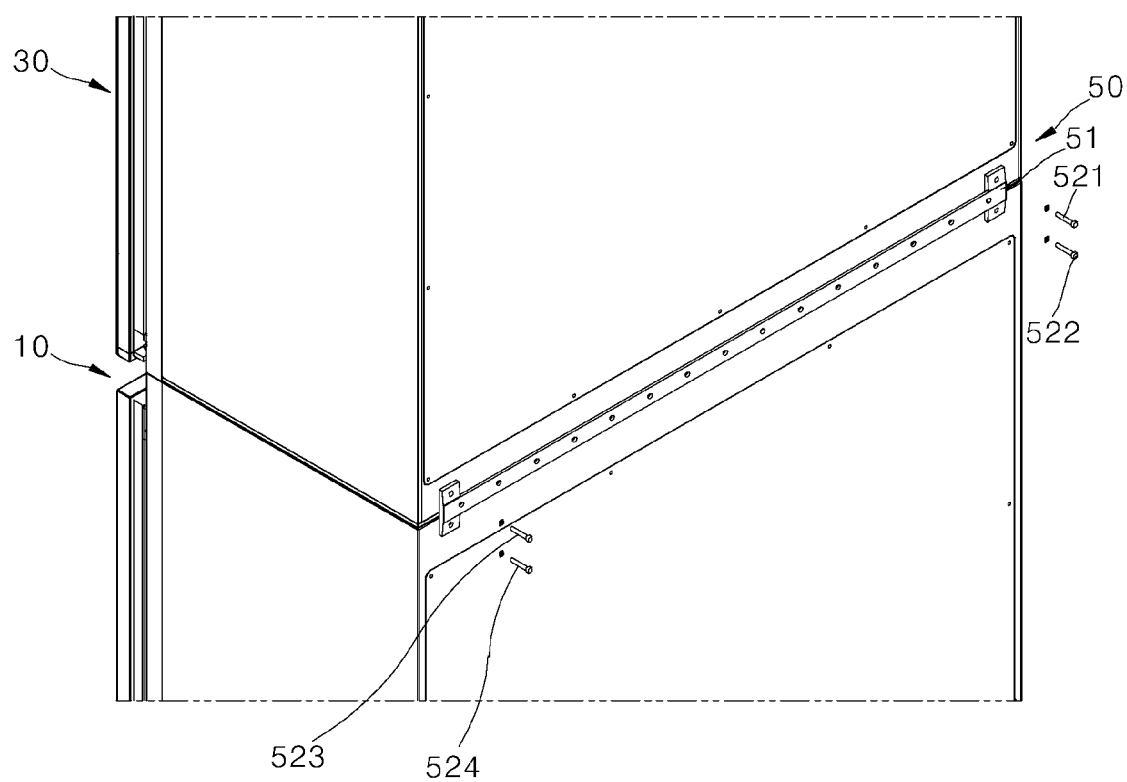

[FIG. 5]
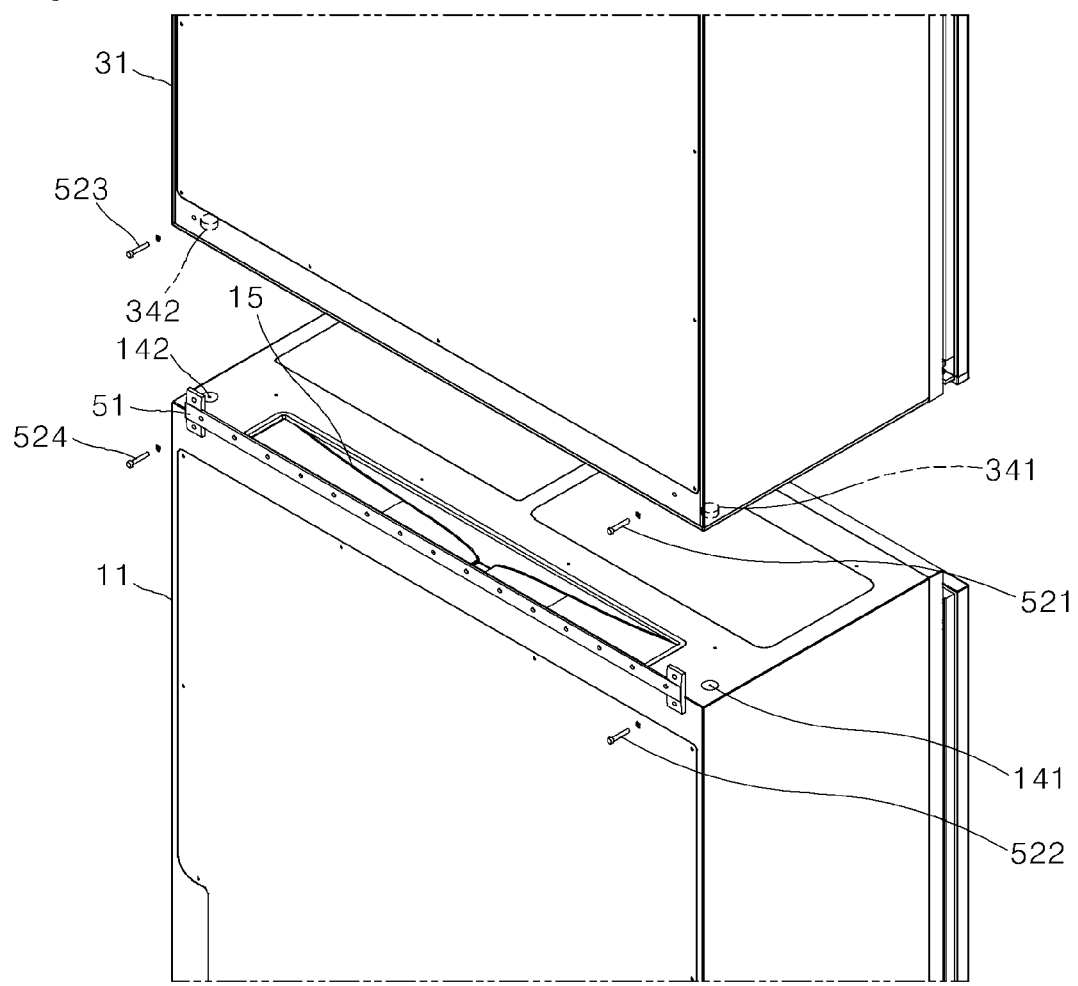

[FIG. 6]
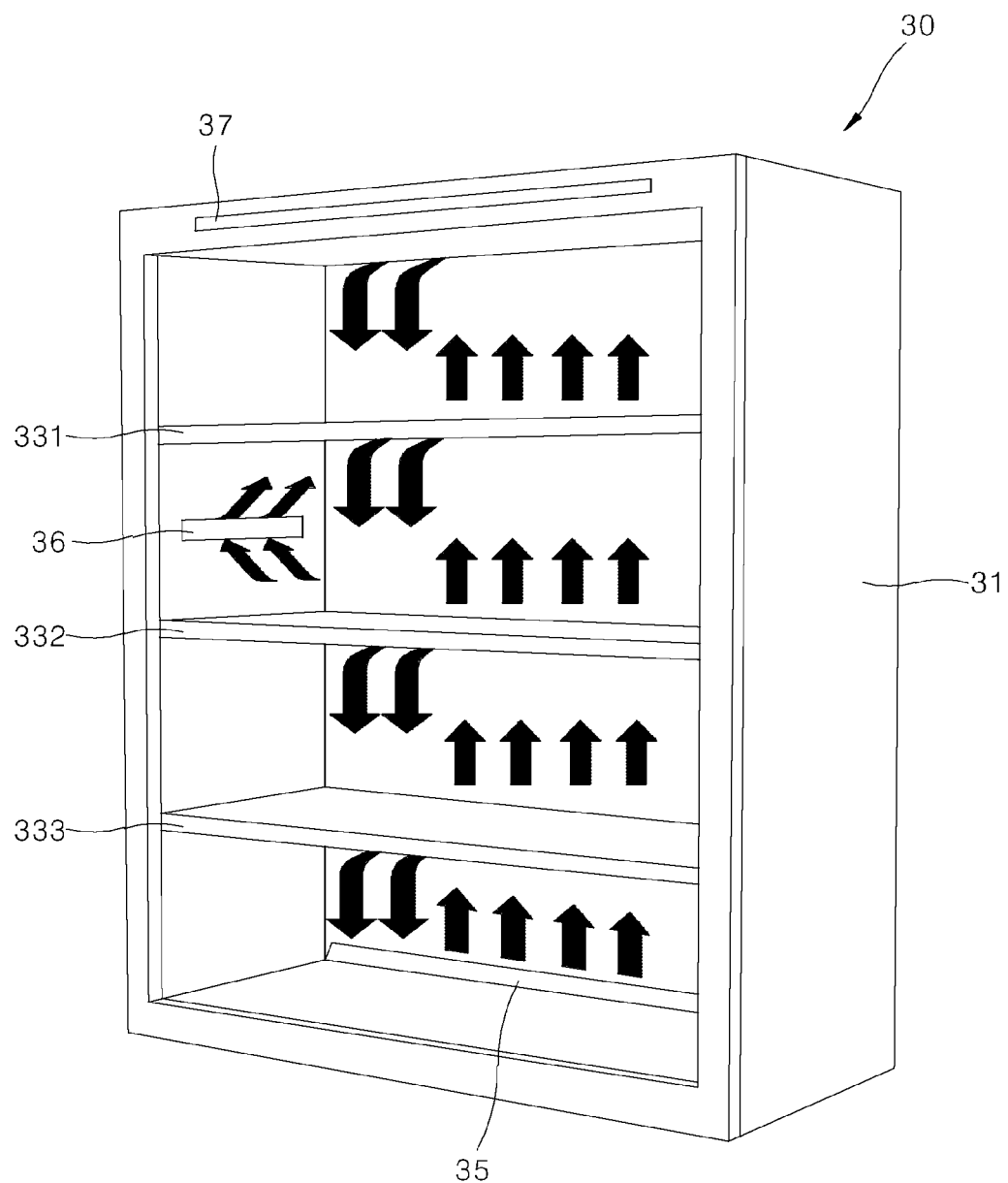

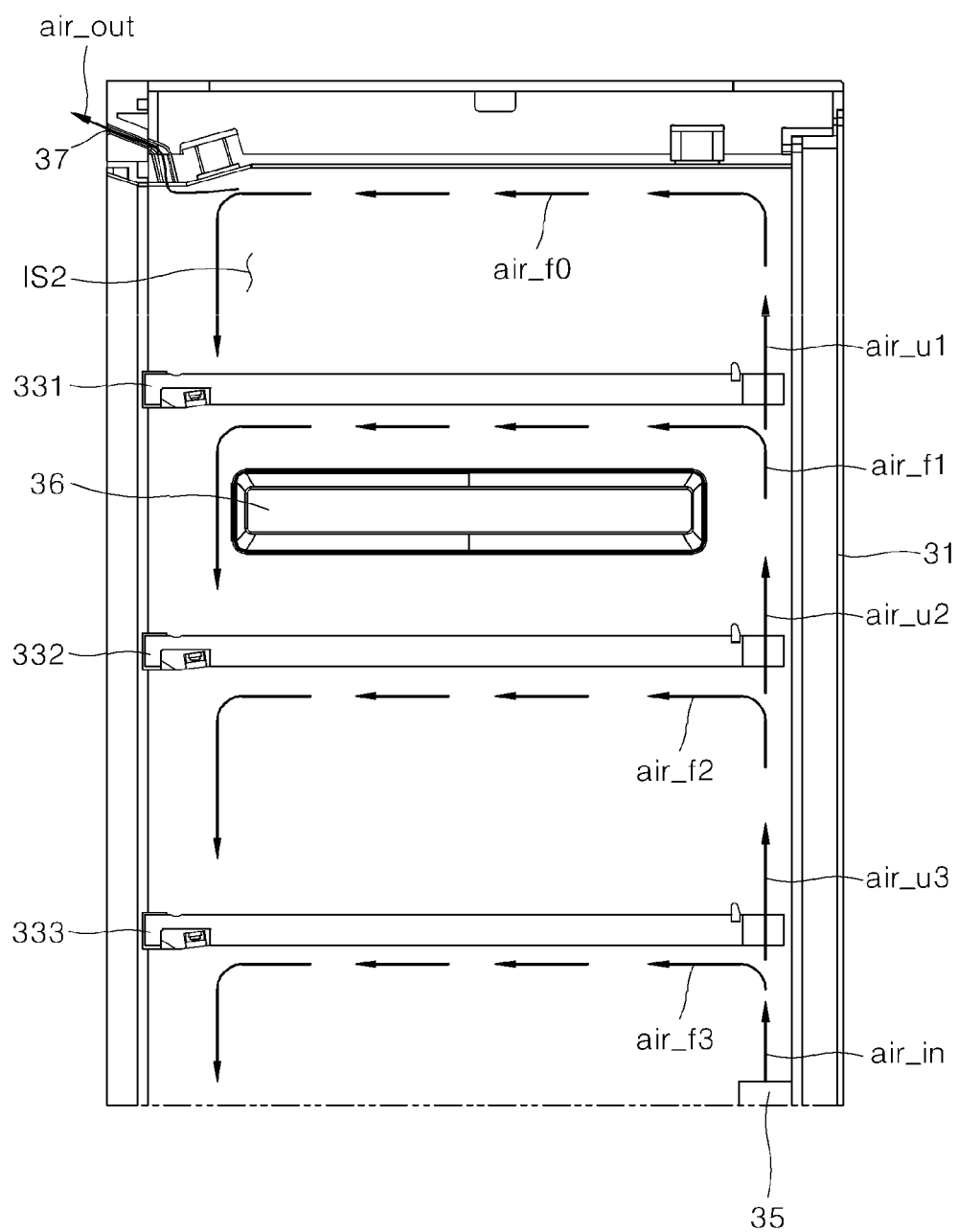

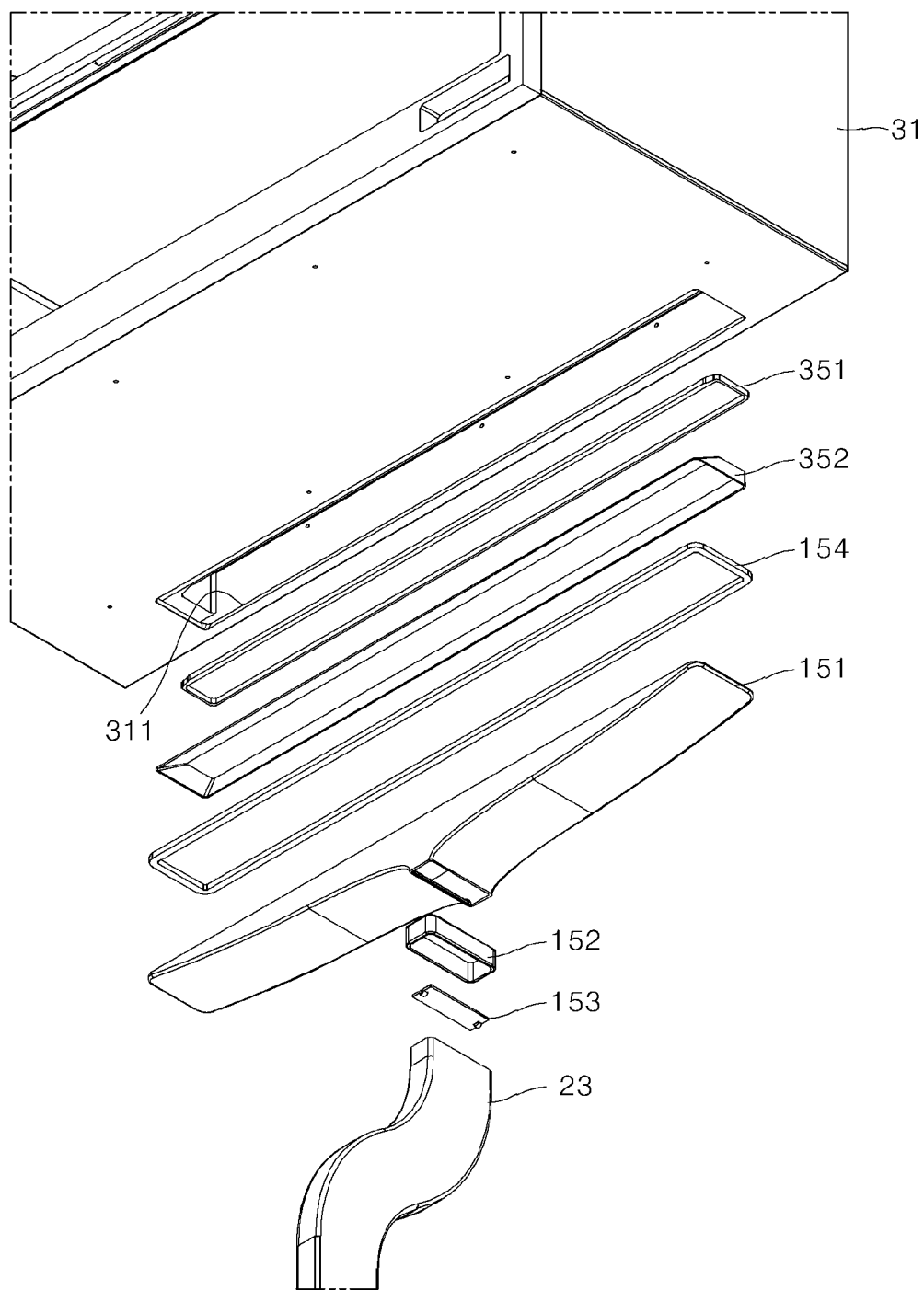
[FIG. 8]

[FIG. 9]
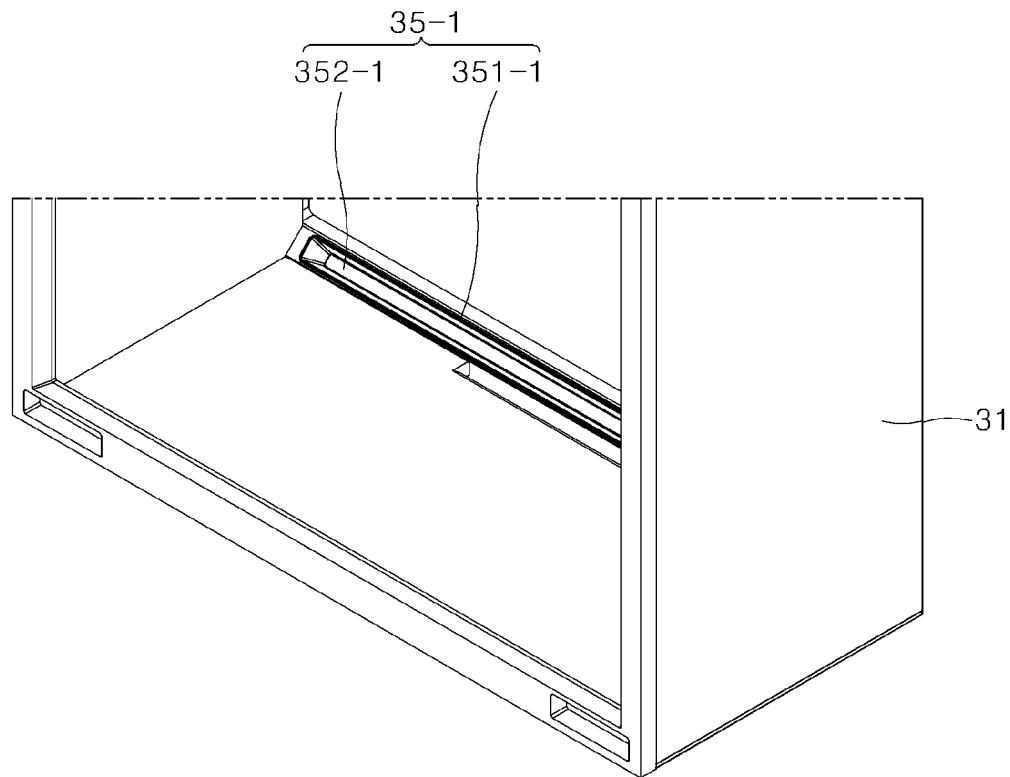
[FIG. 10]
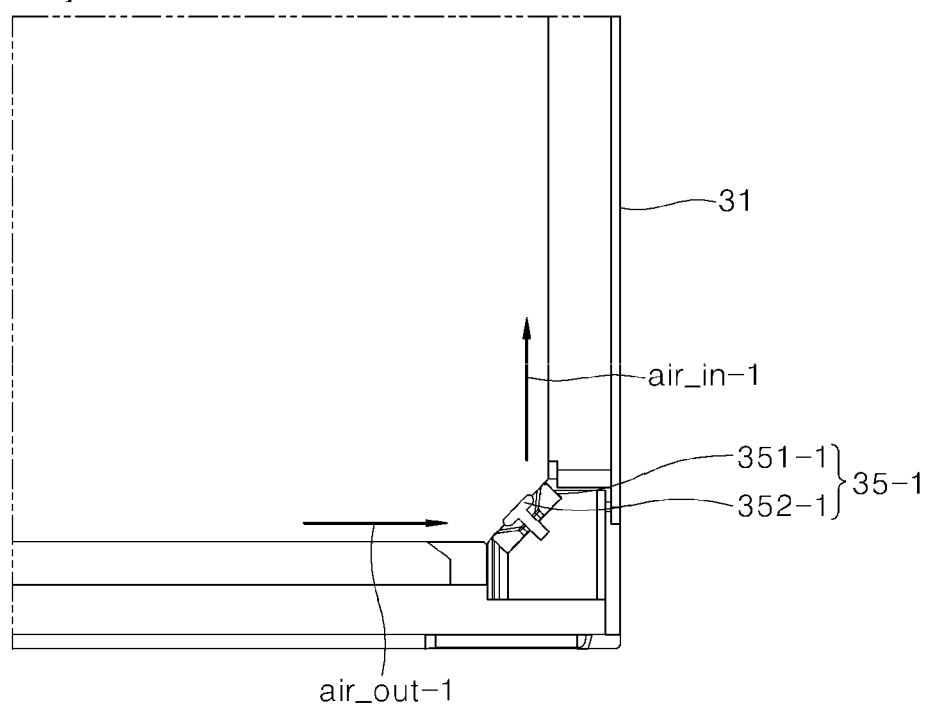

SHOE MANAGEMENT APPARATUS

CROSS-REFERENCE TO RELATED APPLICATION

This application claims priority to and the benefit of Korean Patent Application No. 10-2020-0077410, filed on Jun. 24, 2020, Korean Patent Application No. 10-2020-0077411, filed on Jun. 24, 2020, Korean Patent Application No. 10-2020-77412, filed on Jun. 24, 2020, Korean Patent Application No. 10-2020-0077413, filed on Jun. 24, 2020, Korean Patent Application No. 10-2020-77414, filed on Jun. 24, 2020, Korean Patent Application No. 10-2020-0077415, filed on Jun. 24, 2020, Korean Patent Application No. 10-2020-0077417, filed on Jun. 24, 2020, Korean Patent Application No. 10-2020-0170566, filed on Dec. 8, 2020, and Korean Patent Application No. 10-2021-0031064, filed on Mar. 9, 2021, the disclosures of which are incorporated herein by reference in their entirety into the present application.

BACKGROUND OF THE INVENTION

1. Field of the Invention

The present disclosure relates to a shoe management apparatus that can perform at least one function selected from among storage, sterilization, and decontamination of shoes.

2. Description of the Background Art

Generally, a shoe rack installed in an entrance room of a building is used to hold and organize various types of shoes.

However, when shoes wet with water or sweat are stored in a shoe rack, the humidity inside the shoe rack increases, causing deterioration and reduction in lifespan of all shoes stored therein. In particular, with increasing demand for high-end shoes in recent years, interest is growing in an apparatus that can properly manage shoes to extend lifespan of the shoes.

In addition, shoes are generally used for outdoor activities and thus can be easily contaminated with dust, bacteria, and viruses. Therefore, it is important from the viewpoint of hygiene for households to frequently perform sterilization or decontamination of shoes.

SUMMARY OF THE INVENTION

Embodiments of the present disclosure provide a shoe management apparatus that can more efficiently circulate air in an inner space for storing shoes.

Embodiments of the present disclosure provide a shoe management apparatus that can prevent contamination of an inner space for storing shoes.

Embodiments of the present disclosure provide a shoe management apparatus that can be built-in in an entrance room of a building.

The above and other objects and advantages of the present disclosure will become apparent from the detailed description of the following embodiments in conjunction with the accompanying drawings. In addition, it will be readily understood that the objects and advantages of the present disclosure can be realized by features set forth in the appended claims or combinations thereof.

In accordance with one aspect of the present disclosure, a shoe management apparatus includes an exhaust port through which air is discharged to an inner space for storing shoes and a discharge port through which air is discharged from the inner space, wherein the exhaust port and the discharge port are disposed at diagonally opposite edges of the inner space, respectively.

In an embodiment, the exhaust port may allow air to be laterally diffusely discharged to the inner space therethrough.

In accordance with another aspect of the present disclosure, a shoe management apparatus includes: a cabinet defining an inner space for storing shoes; an exhaust port disposed at a rear lower edge of the inner space and allowing air to be discharged into the inner space therethrough; and a front discharge port disposed at an upper front surface of the cabinet and allowing air to be discharged from the inner space therethrough.

In an embodiment, the exhaust port may have a horizontally elongated rectangular shape.

In an embodiment, the exhaust port may be configured to discharge air upwards therethrough.

In an embodiment, the exhaust port may include an inlet and an exhaust port packing. The inlet may be inserted into a bottom opening formed on a rear bottom surface of the cabinet to guide air into the inner space. The exhaust port packing may be disposed between the inlet and the bottom opening. The exhaust port packing may be formed of an elastic material.

In an embodiment, the shoe management apparatus may further include: at least one partition dividing the inner space into multiple compartments from top to bottom. Wherein, the at least one partition has a rear end, and at least some part of the rear end is spaced apart from an inner surface of the cabinet.

In an embodiment, the shoe management apparatus may further include: a circulation filter disposed on an inner side surface of the cabinet and removing contamination from air introduced through a lower opening thereof and discharged through an upper opening thereof.

In accordance with a further aspect of the present disclosure, a shoe management apparatus includes: a first cabinet defining a first inner space for storing shoes and a space for an electrical room disposed under the first inner space; a first exhaust port disposed on a rear portion of an upper surface of the first cabinet and allowing air introduced from the electrical room to be discharged therethrough; a second cabinet disposed on the upper surface of the first cabinet and defining a second inner space for storing shoes; and a second exhaust port disposed at a rear lower edge of the second inner space and allowing air introduced from the first exhaust port to be discharged into the second inner space therethrough.

In an embodiment, the shoe management apparatus may further include: a front discharge port disposed on an upper front surface of the second cabinet and allowing air to be discharged from the second inner space therethrough.

In an embodiment, the first exhaust port may have a larger area at a point at which air is introduced into the first exhaust port from the electrical room than at a point at which the first exhaust port is connected to the second exhaust port.

The shoe management apparatus according to the present disclosure can more efficiently circulate air in an inner space for storing shoes.

In addition, the shoe management apparatus according to the present disclosure can prevent contamination of the inner space for storing shoes.

The above and other effects of the present disclosure will become apparent from the following detailed description of the present disclosure.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a perspective view of a shoe management apparatus according to an embodiment of the present disclosure.

FIG. 2 is a front view of the shoe management apparatus according to the embodiment of the present disclosure shown in FIG. 1, with doors opened.

FIG. 3 is a perspective view of the shoe management apparatus according to the embodiment of the present disclosure shown in FIG. 1, with the doors and an electric compartment front panel removed therefrom.

FIG. 4 is a partial view of a back surface of the shoe management apparatus according to the embodiment of the present disclosure shown in FIG. 1.

FIG. 5 is a partial view of the shoe management apparatus according to the embodiment of the present disclosure shown in FIG. 1, with a first management apparatus separated from a second management apparatus.

FIG. 6 is a perspective view of the second management apparatus of the shoe management apparatus according to the embodiment of the present disclosure shown in FIG. 1, with doors removed therefrom.

FIG. 7 is a sectional view of the second management apparatus of the shoe management apparatus according to the embodiment of the present disclosure shown in FIG. 6.

FIG. 8 is a view illustrating the configuration of a first exhaust port of the first management apparatus and a second exhaust port of the second management apparatus of the shoe management apparatus according to an embodiment of the present disclosure.

FIG. 9 shows another embodiment of the second exhaust port of the second management apparatus of the shoe management apparatus according to the embodiment of the present disclosure.

FIG. 10 is a view illustrating air flows according to the other embodiment of the second exhaust port shown in FIG. 9.

DETAILED DESCRIPTION

Reference will now be made in detail to various embodiments, examples of which are illustrated in the accompanying drawings such that the present disclosure can be easily implemented by those skilled in the art. Description of known functions and constructions that may unnecessarily obscure the subject matter of the present disclosure will be omitted. Like components will be denoted by like reference numerals throughout the specification.

It will be understood that, although the terms "first," "second," and the like may be used herein to describe various elements and the like, these elements should not be limited by these terms. These terms are only used to distinguish one element from another element. Thus, a first element discussed below could be termed a second element, or vice versa, without departing from the scope of the present disclosure.

It will be understood that when a component is referred to as being disposed "at an upper (lower) portion of" or "on (or "under") another component, it can be directly formed to adjoin an upper surface ("a lower surface") of the other component, or intervening component(s) may also be interposed therebetween.

In addition, when a certain component is referred to as being "connected to," "coupled to" or "joined to" another component, these components may be directly connected to, coupled to or joined to each other or through another component, or intervening component(s) may also be "interposed" therebetween.

As used herein, the singular forms, "a," "an," and "the" are intended to include the plural forms as well, unless the context clearly indicates otherwise. Moreover, the terms "comprises," "comprising," "includes," and/or "including," when used in this specification, should not be construed to mean that a process, method, article, or apparatus comprising a list of elements or steps necessarily comprises all the elements or all the steps. Thus, such a process, method, article, or apparatus may be free from some of the elements or the steps, or may further include one or more other elements or steps.

Hereinafter, a shoe management apparatus according to some exemplary embodiments of the present disclosure will be described.

FIG. 1 is a perspective view of a shoe management apparatus 1 according to an embodiment of the present disclosure. The shoe management apparatus 1 may include a first management apparatus 10 and a second management apparatus 30. The first management apparatus 10 may include a first cabinet 11, a 1st first door 121, and a 2nd first door 122, and the second management apparatus 30 may include a second cabinet 31, a 1st second door 321, and a 2nd second door 322. The shoe management apparatus 1 may further include a display unit 40. The display unit 40 may be an electronic visual display, such as an LCD, TFT-LCD, OLED, a flexible display, and a three-dimensional display.

The first management apparatus 10 may be disposed at a lower portion of the shoe management apparatus 1. The first management apparatus 10 may perform at least one operation selected from among removal of contaminants, such as dust, sterilization, deodorization, dehumidification, drying, and coating for shoes placed therein. Here, the sterilization operation may include at least one selected from among ultraviolet (UV) sterilization and steam sterilization. UV sterilization may be an operation of irradiating the shoes with short-wave UV rays having a wavelength of about 100 nm to 280 nm. Steam sterilization may be an operation of sterilizing the shoes using steam generated by heating water. The steam may be generated by heating water to 100° C. In addition, the generated steam may have a temperature of 40° C. to 50° C.

The first management apparatus 10 may be an apparatus that performs at least two of the aforementioned operations (that is, contaminant removal, sterilization, deodorization, dehumidification, drying, and coating) for a relatively short period of time in order to remove contamination of shoes placed therein. For example, the first management apparatus may sequentially perform removal of contaminants, such as dust, from surfaces of the shoes placed therein, sterilization and deodorization using the short-wave UV rays and a photocatalyst, sterilization using steam, dehumidification and drying, and coating for providing repellency to water for a predetermined period of time (for example, 40 minutes).

That is, the first management apparatus 10 may be referred to as an "intensive care apparatus."

The first cabinet 11 of the first management apparatus 10 may define an exterior of the first management apparatus 10. The first cabinet 11 may be provided in the form of a cuboid open at a front thereof.

The 1st first door 121 and the 2nd first door 122 of the first management apparatus 10 may be disposed at the front of the first cabinet 11.

The second management apparatus 30 may be disposed on an upper surface of the first management apparatus 10. The second management apparatus 30 may perform at least one operation selected from among sterilization, ventilation, and humidity control of a space in which shoes are placed. Here, the sterilization operation may be performed using the short-wave ultraviolet rays described above or a photocatalytic filter.

The second management apparatus 30 may be an apparatus that constantly performs operations necessary for preventing deterioration of shoes stored therein. That is, the second management apparatus 30 may be referred to as a "constant management apparatus" or "light care apparatus".

The second cabinet 31 of the second management apparatus 30 may define an exterior of the second management apparatus 30. The second cabinet 31 may be provided in the form of a cuboid open at a front thereof.

The 1st second door 321 (that is, a first upper door) and the 2nd second door 322 of the second management apparatus may be disposed at the front of the second cabinet 31.

The display unit 40 may display a current operating state, abnormality, or the like of the shoe management apparatus 1. The display unit 40 may be disposed at a lower portion of the 2nd second door 322.

For convenience of description, a side or portion of the shoe management apparatus 1 at which the doors 121, 122, 321, 322 are disposed is defined as "front" and the other side or portion of the shoe management apparatus 1 is defined as "rear".

FIG. 2 is a front view of the shoe management apparatus 1 according to the embodiment of the present disclosure shown in FIG. 1, with the doors opened.

The first management apparatus 10 may be formed at an upper portion thereof with a first inner space IS1 for storing shoes and may include an electric compartment disposed under the first inner space IS1. An electric compartment front panel 201 may be disposed at a front of a space for the electric compartment. That is, the first cabinet 11 may define the first inner space IS1 and the space for the electric compartment, and the front of the electric compartment may be covered by the electric compartment front panel 201.

The space for the electric compartment may contain devices for dehumidifying air in the electric compartment, devices for discharging the dehumidified air to the first inner space IS1 and a second inner space IS2, a water supply container 271, and a drain container 272. The water supply container 271 may be detachably coupled to the first cabinet 11. The water supply container 271 may supply water to a steam generator 26 of the electric compartment 20.

The first management apparatus 10 may include at least one first partition dividing the first inner space IS1 into multiple compartments. The first partition may include a partition dividing the first inner space IS1 from side to side.

As in this embodiment, the first inner space IS1 may be divided by a 1st first partition 131, a 2nd first partition 132, and a 3rd first partition 133. The 1st first partition 131 may divide the first inner space IS1 from side to side. The 1st first partition 131 may be disposed at a center of the first inner space IS1 with reference to the side-to-side direction. Each of the 2nd first partition 132 and the 3rd first partition 133 may divide the first inner space IS1 from top to bottom.

The second management apparatus 30 may be formed with a second inner space IS2 for storing shoes. That is, the second cabinet 31 may define the second inner space IS2 for storing shoes.

The second management apparatus 30 may include at least one second partition dividing the second inner space IS2 into multiple compartments. The second partition may include at least one partition dividing the second inner space IS2 from top to bottom.

As in this embodiment, the second inner space IS2 may be divided from top to bottom by a 1st second partition 331, a 2nd second partition 332, and a 3rd second partition 333.

FIG. 3 is a perspective view of the shoe management apparatus 1 according to the embodiment of the present disclosure shown in FIG. 1, with the doors 121, 122, 321, 322 and the electric compartment front panel 201 removed therefrom. In FIG. 3, arrows indicate air flow directions.

As described above, the electric compartment 20 is disposed at a lower portion of the first management apparatus 10. The electric compartment 20 may be formed separately from the first management apparatus 10 or may be formed integrally with the first management apparatus 10. Herein, the present disclosure will be described with reference to an example in which the electric compartment 20 is formed integrally with the first management apparatus 10.

The electric compartment 20 may force a fluid to flow in or out of the electric compartment. That is, the electric compartment 20 may supply the fluid to the first inner space IS1 and/or the second inner space IS2. Alternatively, the electric compartment 20 may draw in the fluid from the first inner space IS1 and/or the second inner space IS2. Here, the fluid may be air, steam, or a material containing substances necessary for management of shoes.

The electric compartment 20 draws in air, dehumidifies the drawn-in air, and discharges the dehumidified air. The electric compartment 20 may include a main fan 21 that draws in air, dehumidifies the drawn-in air, and discharges the dehumidified air. The electric compartment 20 may further include a housing 25 and a steam generator 26 that generates steam by heating water. The steam generator 26 may heat water to 100° C. The housing 25 may define a space for drying and/or heating air. The housing 25 may be formed on an upper surface thereof with an opening 251 through which air is introduced into the housing, may be formed therein with a space for accommodating a heat pump (more specifically, a condenser and/or an evaporator of the heat pump), and may be formed on a side surface thereof with an opening connected to the main fan 21 (specifically, a housing 25 of the main fan).

The air discharged from the electric compartment 20 may be delivered to the first inner space IS1 of the first management apparatus 10 and/or the second inner space IS2 of the second management apparatus 30. To this end, the shoe management apparatus may be formed with a first fluid path communicating between the main fan in the electric compartment 20 and the first inner space IS1 and a second fluid path communicating between the main fan in the electric compartment 20 and the second inner space IS2.

The air inside the first inner space IS1 may be drawn back into the electric compartment. To this end, the shoe management apparatus may be formed with a return fluid path extending through the first inner space IS1 and the electric compartment 20.

The second management apparatus 30 may include a second exhaust port 35 through which the air delivered from the electric compartment 20 is discharged to the second inner space IS2. The second exhaust port 35 may be disposed at a rear bottom of the second inner space IS2 defined by the second cabinet 31, but the second exhaust port 35 may be disposed on any portion of a bottom surface of the second inner space IS2.

In addition, the second management apparatus 30 may include a circulation filter 36 removing harmful substances from the air inside the second inner space IS2. The circulation filter 36 may be disposed on an inner side surface of the second cabinet 31. Although one circulation filter 36 is shown in FIG. 3, it will be understood that the present disclosure is not limited thereto and the second management apparatus 30 may include multiple circulation filters 36. For example, another circulation filter may be disposed opposite the circulation filter 36 shown in FIG. 3.

In addition, the second management apparatus 30 may include a front discharge port 37 through which air in the second inner space IS2 is discharged to an outside of the shoe management apparatus. The front discharge port 37 may be disposed on an upper front surface of the second cabinet 31 or any outer surface of the second cabinet 31.

In addition, at least one of the partitions 331, 332, 333 of the second management apparatus 30 may be variable in angle with respect to a front-to-rear direction of the shoe management apparatus. That is, at least one of the partitions 331, 332, 333 of the second management apparatus 30 may be movable so as to be positioned at various different angles. When the multiple partitions are configured to be variable in angle with respect to the front-to-rear direction, each of the multiple partitions may be independently variable in angle with respect to the front-to-rear direction. With the configuration in which at least one of the partitions 331, 332, 333 is variable in angle with respect to the front-to-rear direction, the air in the second inner space IS2 can flow in various forms, thereby securing uniform ventilation throughout the second inner space IS2, including corners thereof.

As shown in FIG. 1, FIG. 2 and FIG. 3, the shoe management apparatus 1 according to the embodiment of the present disclosure may include: the first management apparatus including the electric compartment 20 and formed with the first inner space IS1 for storing shoes; and the second management apparatus 30 disposed on the upper surface of the first management apparatus 10 and formed with the second inner space IS2 for storing shoes. The electric compartment 20 may be disposed at the lower portion of the first management apparatus 10, and the first inner space IS1 may be formed on an upper side of the space for the electric compartment 20. The first management apparatus 10 may perform at least one operation selected from among contaminant removal, sterilization, deodorization, dehumidification, drying, and coating for shoes placed in the first inner space IS1 with relatively high intensity for a relatively short period of time (or any intensity level for any amount of time), and the second management apparatus 30 may perform at least one operation selected from among sterilization, ventilation, and dehumidification of the second inner space IS2 with relatively low intensity for a relatively long period of time (or with any intensity level for any amount of time), the intensity of the at least one operation of the second management apparatus 30 is less than the intensity of the at least one operation of the first management apparatus 10.

Here, "relatively high intensity" means that the temperature of the steam used in the sterilization operation is relatively high, the intensity of the UV rays used in the sterilization operation is relatively high, or the intensity of the airflow applied to shoes is relatively high.

As such, the shoe management apparatus according to this embodiment of the present disclosure can quickly remove contamination of shoes while allowing long-term storage of shoes without deterioration of the shoes. In addition, the shoe management apparatus according to this embodiment of the present disclosure can be built-in in an entrance room of a building due to structural compactness thereof.

In addition, according to this embodiment of the present disclosure, dehumidified air can be supplied to two management apparatuses using one electric compartment. Thus, it is possible to reduce the overall size of the shoe management apparatus.

FIG. 4 is a partial view of a back surface of the shoe management apparatus according to the embodiment of the present disclosure shown in FIG. 1. Referring to FIG. 4, the shoe management apparatus may include a longitudinal fastener 50 coupling the first management apparatus 10 to the second management apparatus 30. The longitudinal fastener 50 may include a longitudinal connection bar 51 and multiple longitudinal connection screws 521, 522, 523, 524.

Referring to FIG. 4, the shoe management apparatus according to the embodiment of the present disclosure may have a structure in which the first management apparatus 10 and the second management apparatus 30 are stacked vertically (i.e., in a vertical direction).

The longitudinal fastener 50 may couple the stacked first management apparatus 10 and second management apparatus 30 to each other. The longitudinal fastener 50 may be disposed on the back surface (i.e., rear surface) of the shoe management apparatus 1.

The longitudinal connection bar 51 may be disposed at a joint between the first management apparatus 10 and the second management apparatus 30 to be partially located on a back surface of the first management apparatus 10 and partially located on a back surface (i.e., rear surface) of the second management apparatus 30. The longitudinal connection bar 51 may have a horizontally elongated "H" shape, as viewed from behind the shoe management apparatus.

The longitudinal connection screws 521, 522, 523, 524 serve to securely couple the connection bar 51 to the first management apparatus 10 or the second management apparatus 30. Specifically, the longitudinal connection screws 521, 523 may couple the longitudinal connection bar 51 to the second management apparatus 30, and the longitudinal connection screws 522, 524 may couple the longitudinal connection bar 51 to the first management apparatus 10. When viewed from behind the shoe management apparatus, the longitudinal connection screws 521, 522 may be disposed on the right and the connection screws 523, 524 may be disposed on the left.

FIG. 5 is a partial view of the shoe management apparatus 1 according to the embodiment of the present disclosure shown in FIG. 1, with the first management apparatus 10 separated from the second management apparatus 30.

The first cabinet 11 of the first management apparatus 10 may include first signal contacts 141, 142 disposed on the upper surface thereof. In addition, the second cabinet 31 of the second management apparatus 30 may include second signal contacts 341, 342 disposed on the lower surface thereof.

Upon stacking the second management apparatus 30 on the upper surface of the first management apparatus 10, the first signal contacts 141, 142 may contact the second signal contacts 341, 342, respectively. The first management apparatus 10 may exchange necessary signals (data) with the second management apparatus 30 through signal transmission via the first signal contacts 141, 142 and the second signal contacts 341, 342. The signal transmission may be a wireless transmission, such as Bluetooth™, Zigbee™, Wi-Fi, etc.

In addition, the first management apparatus 10 may include a first exhaust port 15 disposed at an upper end thereof (i.e., the upper surface). Upon stacking the second management apparatus 30 on the upper surface of the first management apparatus 10, the first exhaust port 15 may be connected to the second exhaust port 35 of the second management apparatus 30. In this way, the air delivered from the electric compartment 20 can be discharged into the second inner space IS2 through the first exhaust port 15 of the first management apparatus 10 and through the second exhaust port 35 of the second management apparatus 30.

In an embodiment, the first management apparatus 10 may be used alone in the shoe management apparatus 1, unlike in the embodiments shown in FIG. 1 to FIG. 5. In this embodiment, the first exhaust port 15 may be used to dehumidify a space in which the shoe management apparatus 1 is installed (for example, an entrance room of a building).

FIG. 6 is a perspective view of the second management apparatus 30 of the shoe management apparatus 1 according to an embodiment of the present disclosure shown in FIG. 1, with the doors removed therefrom, and is provided to illustrate circulation of air in the second management apparatus 30. In FIG. 6, arrows indicate air flow routes.

The second exhaust port 35 may be disposed at a rear bottom edge of the second cabinet 31 of the second management apparatus 30. The second exhaust port 35 may be configured to discharge air upwards therethrough.

In addition, the second exhaust port 35 may have a horizontally elongated rectangular shape. That is, the second exhaust port 35 may be narrow in width and long in length. Accordingly, air can be discharged from the second exhaust port 35 in a narrow and long shape. In this way, the air discharged from the second exhaust port 35 can more easily flow to an upper end of the second inner space IS2 defined by the second cabinet 31.

In addition, as described above, at least one of the second partitions 331, 332, 333 may be variable in angle with reference to the front-rear direction. In this way, the flow of air in the second inner space IS2 can become more active and diverse.

The second cabinet 31 may include a circulation filter 36 disposed on an inner wall thereof. The circulation filter 36 may be configured to allow air to flow in from below and to flow out upwards. In an embodiment, the shoe management apparatus may further include a small fan disposed inside the circulation filter 36 to facilitate air circulation through the circulation filter 36.

The second cabinet 31 may include a front discharge port 37 formed on an upper front surface thereof. The front discharge port 37 is configured to discharge air from the second inner space IS2 to the outside of the shoe management apparatus 1 therethrough.

FIG. 7 is a sectional view of the second management apparatus of the shoe management apparatus according to the embodiment of the present disclosure shown in FIG. 6, illustrating air circulation in the second management apparatus 30. In FIG. 7, arrows indicate air flow routes.

At least some of the second partitions 331, 332, 333 may have a rear end at least partially spaced apart from the inner surface of the second cabinet 31.

According to an embodiment of the present disclosure, each time air (air_in) introduced into the second inner space IS2 through the second exhaust port 35 hits the rear end of each of the second partitions 331, 332, 333, some portion of the air (air_f1, air_f2, air_f3) flows forwards along a lower surface of each of the second partitions and the other portion of the air (air_u1, air_u2, or air_u3) flows upwards through a space between the rear end of each of second partitions 331, 332, 333 and the inner surface of the second cabinet 31.

In addition, among the air flowing in the second inner space defined by the second cabinet 31, air (air_u1) that has moved to an uppermost layer of the second inner space (that is, air that has passed through a space between the 1st second partition 331 and the second cabinet 31) flows forwards (air_f0) along an upper inner surface of the second cabinet 31 and then is partially discharged (air_out) to the outside of the shoe management apparatus through the front discharge port 37.

That is, according to the embodiment of the present disclosure, a point at which air is introduced into the second inner space IS2 may be diagonal to a point at which air is discharged from the second inner space IS2. More specifically, as shown in FIG. 6, air may be introduced into the second inner space IS2 through the rear lower edge of the second inner space IS2 and may be discharged from the second inner space IS2 through the front upper edge of the second inner space IS2. With this structure, air can flow over substantially the entire region of the second inner space IS2.

In addition, according to an embodiment of the present disclosure, the second exhaust port 35 may be short in the side-to-side direction and long in the front-to-rear direction (or may have any dimension), and at least some of the second partitions 331, 332, 333 may have a rear end, and at least some part of the rear end is spaced apart from the inner surface of the second cabinet 31. In this way, a larger amount of air can be moved to the upper end of the second inner space IS2.

In addition, according to an embodiment of the present disclosure, at least some of the second partitions 331, 332, 333 may be variable in angle with respect to the front-to-rear direction. In this way, air can flow in different forms in different compartments partitioned off by the second partitions 331, 332, 333, thereby improving ventilation and dehumidification efficiency.

FIG. 8 shows the configuration of the first exhaust port 15 of the first management apparatus 10 and the second exhaust port 35 of the second management apparatus 30 of the shoe management apparatus according to an embodiment of the present disclosure. The first exhaust port 15 may include a diffuser 151, a first exhaust port lower packing 152, a control damper 153, and a first exhaust port upper packing 154. The second exhaust port 35 may include a second exhaust port packing 351 and a second inlet 352. In FIG. 8, reference numeral 23 denotes a longitudinal connection pipe guiding air discharged from the electric compartment (20 of FIG. 2) to the first exhaust port 15. The longitudinal connection pipe may vertically extend through the inside of the 1st first partition (131 of FIG. 2) of the first management apparatus 10.

The diffuser 151 may have a smaller cross-sectional area at an air inlet point thereof and a larger cross-sectional area at an air outlet point to diffuse air discharged therethrough. The diffuser 151 may be disposed at the rear upper end of the first cabinet 11 of the first management apparatus 10.

The first exhaust port lower packing 152 may be disposed between the longitudinal connection pipe 23 and the diffuser 151. The first exhaust port lower packing 152 may be formed of an elastic material, such as rubber. The first exhaust port lower packing 152 prevents air leakage through a gap between the longitudinal connection pipe 23 and the diffuser 151.

The control damper 153 may be disposed at the air inlet point of the diffuser 151. For example, the control damper 153 may be disposed at a joint between the diffuser 151 and the longitudinal connection pipe 23. The control damper 153 serves to adjust the flow rate of air discharged through the diffuser 151. That is, the control damper 153 may be operable to selectively supply air to the second inner space IS2.

The first exhaust port upper packing 154 may be disposed between the diffuser 151 and a first top opening formed on the upper surface of the first cabinet 11, the first top opening being configured to dispose the first exhaust port 15 therein. The first exhaust port lower packing 154 may be formed of an elastic material such as rubber. The first exhaust port upper packing 154 prevents air leakage through a gap between the first cabinet 11 and the diffuser 151. In addition, the first exhaust port upper packing 154 may also serve to maintain airtightness between the first exhaust port 15 (more specifically, the diffuser 151) and the second exhaust port 35 (more specifically, a second inlet 352) with the second management apparatus 30 disposed on the upper surface of the first management apparatus 10.

The second exhaust port packing 351 may be disposed between the second inlet 352 and a second bottom opening 311 formed on the bottom surface of the second cabinet 31 and configured to dispose the second exhaust port 35 therein. The second exhaust port packing 351 may be formed of an elastic material, such as rubber. The second exhaust port packing 351 prevents air leakage through a gap between the second cabinet 31 and the second inlet 352. In addition, the second exhaust port packing 351 may also serve to maintain airtightness between the first exhaust port 15 (more specifically, the diffuser 151) and the second exhaust port 35 (more specifically, the second inlet 352) with the second management apparatus 30 disposed on the upper surface of the first management apparatus 10.

The second inlet 352 may be disposed at a rear bottom of the second cabinet 31. The second inlet 352 may be inserted into the second bottom opening 311 formed in the second cabinet 31. The second inlet 352 guides air delivered from the first exhaust port 15 to the second inner space IS2 defined by the second cabinet 31.

FIG. 9 shows another embodiment of the second exhaust port of the second management apparatus of the shoe management apparatus according to the present disclosure. Referring to FIG. 9, a second exhaust port 35-1 according to this embodiment may include a second duct 351-1 and a second airflow divider 352-1.

The second exhaust port 35-1 may be disposed at a rear lower edge of an interior (that is, the second inner space IS2) of the second cabinet 31.

The second duct 351-1 may be inserted into the second bottom opening 311 described above with reference to FIG. 8. The second duct 351-1 may guide air delivered from the electric compartment (20 of FIG. 3) to the second inner space IS2 and may guide air in the second inner space IS2 to the electric compartment (20 of FIG. 3).

The second airflow divider 352-1 may divide an airflow moving from the electric compartment 20 to the second inner space IS2 from an airflow moving from the second inner space IS2 to the electric compartment 20.

FIG. 10 is a view illustrating air flow directions according to the other embodiment of the second exhaust port shown in FIG. 9.

As described above, the second airflow divider 352-1 may divide an airflow introduced into the second inner space IS2 from an airflow discharged from the second inner space IS2. More specifically, the second airflow divider 352-1 allows an airflow moving from the electric compartment 20 to the second inner space IS2 to be formed along a rear inner surface of the second cabinet 32 (air_in-1) and allows an airflow moving from the second inner space IS2 to the electric compartment 20 to be formed along a lower inner surface of the second cabinet 31 (air_out-1).

Although some exemplary embodiments have been described herein, it should be understood by those skilled in the art that these embodiments are given by way of example only, and that various modifications, variations, and alterations can be made without departing from the spirit and scope of the present disclosure. In addition, although advantageous effects provided by a certain configuration are not clearly described in description of the exemplary embodiments, it should be noted that expectable effects of the corresponding configuration should be acknowledged.

What is claimed is:

1. A shoe management apparatus, comprising:
   a first cabinet including:
      a first inner space for storing shoes; and
      an electric compartment disposed under the first inner space and configured to discharge air;
   a first exhaust port disposed on an upper surface of the first cabinet and configured to:
      receive air discharged from the electric compartment, and
      discharge the received air;
   a second cabinet disposed on the upper surface of the first cabinet and including a second inner space for storing shoes; and
   a second exhaust port disposed at a rear lower edge of the second inner space and configured to:
      receive air from the first exhaust port, and
      discharge the received air into the second inner space,
   wherein the first exhaust port includes a diffuser, the diffuser including an inlet facing the first cabinet and an outlet facing the second cabinet, and
   wherein the diffuser has a shape that expands in cross-sectional area from the inlet to the outlet.

2. The shoe management apparatus according to claim 1, further comprising a front discharge port disposed on an upper front surface of the second cabinet and configured to discharge air from the second inner space to outside of the shoe management apparatus.

3. The shoe management apparatus according to claim 1, wherein the first exhaust port further includes a control damper disposed at the inlet of the diffuser and configured to adjust a flow rate of air discharged through the diffuser.

4. The shoe management apparatus according to claim 1, wherein the second exhaust port comprises:
   an inlet disposed in a bottom opening of the second cabinet to guide air discharged from the first exhaust port to the second inner space; and
   a second exhaust port packing disposed between the inlet of the second exhaust port and the bottom opening.

5. The shoe management apparatus according to claim 1, further comprising:

at least one first partition vertically dividing the first inner space into multiple compartments; and at least one second partition vertically dividing the second inner space into multiple compartments, the at least one second partition including a rear end at least partially spaced apart from an second inner surface of the second cabinet.

6. The shoe management apparatus according to claim 5, wherein the second exhaust port is configured to discharge air between the rear end of the at least one second partition and the inner surface of the second cabinet.

7. A shoe management apparatus, comprising:
a first cabinet including:
a first inner space for storing shoes; and
an electric compartment disposed under the first inner space and configured to discharge air;
a first exhaust port disposed on an upper surface of the first cabinet and configured to:
receive air discharged from the electric compartment, and
discharge the received air;
a second cabinet disposed on the upper surface of the first cabinet and including a second inner space for storing shoes; and
a second exhaust port disposed at a rear lower edge of the second inner space and configured to:
receive air from the first exhaust port, and
discharge the received air into the second inner space,
wherein the second exhaust port is disposed at a rear edge surface of the second inner space and includes a duct and an airflow divider, and
wherein the airflow divider is configured to direct airflow received by the second exhaust port in a different direction than air discharged by the second exhaust port.

8. A shoe management apparatus, comprising:
a first cabinet including:
a first inner space for storing shoes; and
an electric compartment disposed under the first inner space and configured to discharge air;
a first exhaust port disposed on an upper surface of the first cabinet and configured to:
receive air discharged from the electric compartment, and
discharge the received air;
a second cabinet disposed on the upper surface of the first cabinet and including a second inner space for storing shoes;
a second exhaust port disposed at a rear lower edge of the second inner space and configured to:
receive air from the first exhaust port,
discharge the received air into the second inner space; and
a circulation filter disposed on an inner side surface of the second cabinet, including a lower opening and an upper opening, and configured to:
filter air within the second inner space of the second cabinet introduced through the lower opening of the circulation filter, and
discharge air through the upper opening of the circulation filter.

9. A shoe management apparatus, comprising:
a first cabinet including:
a first inner space for storing shoes;
at least one first partition vertically dividing the first inner space into multiple compartments;
an electric compartment disposed under the first inner space and configured to discharge air; and
a first exhaust port disposed on an upper surface of the first cabinet and configured to:
receive air discharged from the electric compartment, and
discharge the received air;
a second cabinet disposed on the upper surface of the first cabinet and including:
a second inner space for storing shoes;
a second exhaust port disposed at a rear lower edge of the second inner space and configured to:
receive air from the first exhaust port, and
discharge the received air into the second inner space; and
at least one second partition vertically dividing the second inner space into multiple compartments, the at least one second partition including a rear end at least partially spaced apart from an inner surface of the second cabinet,
wherein the first exhaust port includes a diffuser, the diffuser including an inlet facing the first cabinet and an outlet facing the second cabinet, and
wherein the diffuser has a shape that expands in cross-sectional area from the inlet to the outlet.

10. The shoe management apparatus according to claim 9, wherein the second exhaust port is configured to discharge air between the rear end of the at least one second partition and the inner surface of the second cabinet.

11. The shoe management apparatus according to claim 9, wherein the first exhaust port further includes a control damper disposed at the inlet of the diffuser and configured to adjust a flow rate of air discharged through the diffuser.

* * * * *